(12) United States Patent
Heider et al.

(10) Patent No.: US 6,264,818 B1
(45) Date of Patent: Jul. 24, 2001

(54) ELECTROCHEMICAL SYNTHESIS OF PERFLUOROALKYLFLUOROPHOSPHORANES

(75) Inventors: Udo Heider, Crumstadt; Volker Hilarius, Gross-Umstadt; Peter Sartori, Rheinberg; Nikolai Ignatiev, Duisburg, all of (DE)

(73) Assignee: Merck Patent Gesellschaft Mit Beschrankter Haftung, Darmstadt (DE)

( * ) Notice: Subject to any disclaimer, the term of this patent is extended or adjusted under 35 U.S.C. 154(b) by 0 days.

(21) Appl. No.: 09/509,013

(22) PCT Filed: Sep. 29, 1999

(86) PCT No.: PCT/EP99/07214

§ 371 Date: May 26, 2000

§ 102(e) Date: May 26, 2000

(87) PCT Pub. No.: WO00/21969

PCT Pub. Date: Apr. 20, 2000

(30) Foreign Application Priority Data

Oct. 9, 1998 (DE) .............................. 198 46 636

(51) Int. Cl.$^7$ ...................................... C25B 3/08
(52) U.S. Cl. ............................................. 205/430
(58) Field of Search ............................... 205/430

(56) References Cited

U.S. PATENT DOCUMENTS 4,900,854  2/1990  Winterton .............................. 556/70

FOREIGN PATENT DOCUMENTS 8803331  5/1988  (WO) .
9427335  11/1994  (WO) .

OTHER PUBLICATIONS

N.V. Pavlenko: "Reaction of tris(perfuoroalkyl)phosphine oxides and tris (perfluoroalkyl) difluorophoshoranes with fluoride ion" Journal of General Chemistry USSR., Bd. 59, Nr. 3, Aug. 30, 1989.

*Primary Examiner*—Edna Wong
(74) *Attorney, Agent, or Firm*—Millen, White, Zelano & Branigan, P.C.

(57) ABSTRACT

The invention relates to a process for preparing perfluoroalkylfluorophosphoranes of the general formula $$(C_nF_{2n+m})_yPF_{5-y} \qquad (I)$$

where
n is 1, 2, 3, 4, 5, 6, 7 or 8
m is +1 or −1 and
y is 1, 2 or 3,
where the ligands ($C_nF_{2n+m}$) may be identical or different, and also to their use as electrolytes and as precursors for conducting salts, and to their employment in lithium batteries.

7 Claims, No Drawings

ELECTROCHEMICAL SYNTHESIS OF PERFLUOROALKYLFLUOROPHOSPHORANES

The invention relates to a process for preparing perfluoroalkylfluorophosphoranes of the general formula $$(C_nF_{2n+m})_yPF_{5-y} \quad (I)$$

where n is 1, 2, 3, 4, 5, 6, 7 or 8 m is +1 or −1 and y is 1, 2 or 3, where the ligands ($C_nF_{2n+m}$) may be identical or different, and also to their use as electrolytes and as precursors for conducting salts, and to their employment in lithium batteries.

Perfluoroalkylfluorophosphoranes are of widespread interest as starting materials for synthesizing a variety of organofluorophosphorus compounds (N. V. Pavlenko et. al., Zh. Obshch. Khim. (Russ.) 1989, Vol. 59, 534–537).

Perfluoroalkylfluorophosphoranes may be synthesized in a variety of ways, e.g. starting from elemental phosphorus and perfluoroalkyl iodides (F. W. Bennett et. al., J. Chem. Soc. 1953, 1565–1571). This reaction normally leads initially to the formation of a complex mixture of mono-, bis- and trisperfluoroalkylphosphanes, which can then be converted by chlorination and fluorination processes into the corresponding phosphoranes (M. Görg et. al., J. Fluorine Chem. 1996, Vol. 79, 103–104). A variety of by-products are produced by the side reactions, and these are difficult to remove and dispose of. One of the disadvantages of this synthetic route is the reaction in the presence of Hg, which remains detectable in the downstream products. Products prepared by this process are unsuitable for use in batteries. In addition, only small laboratory-scale batches can be prepared.

A relatively new method (J. J. Kampa et. al., Angew. Chem. 1995, Vol. 107, 1334–1337) for synthesizing trisperfluoroalkyldifluorophosphoranes is to react elemental fluorine with the corresponding alkyl phosphanes. The disadvantages of this method are complicated operation and very expensive starting materials. The fluorinated solvents needed for the process are expensive to prepare, special safety precautions have to be taken when they are used, and they are expensive to dispose of once used.

The most convenient method known hitherto is the electrochemical fluorination of trialkylphosphine oxides described in DE 26 20 086, using Simons' electrochemical fluorination. The disadvantages of the process are that only trisperfluoroalkylphosphoranes can be prepared and that the yields, from 40 to 50%, are low and decrease still further as the chain length of the alkyl radical rises. Another disadvantage is the unavoidable parallel formation of toxic and explosive by-products, e.g. oxygen difluoride.

The methods known hitherto for obtaining perfluoroalkylphosphoranes by electrochemical fluorination require the presence of strongly electro-negative substituents, such as fluorine or chlorine, or of oxygen, to stabilise the electrofluorination starting materials with respect to the operating medium (DE 19641138 and WO 98/15562). This is confirmed in the literature (Journal of Fluorine Chemistry 75, 1995, 157–161).

The object of the present invention is therefore to provide a cost-effective process which is simple to carry out and which gives the perfluoroalkylfluorophosphoranes in improved yields and high purities, so that the products prepared are suitable for employment in battery electrolytes.

Another object of the invention is to provide a process which avoids the formation of toxic and explosive by-products.

The object of the invention is achieved by electrochemical fluorination of alkylphosphoranes or of alkylphosphanes of the general formula (II) with identical or different alkyl substituents on the phosphorus. This permits the synthesis of cyclic, linear and branched perfluoroalkylphosphoranes of the general formula (I) from compounds of the general formula (II) in high yields by the following reaction scheme

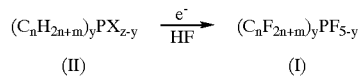

where n is 1, 2, 3, 4, 5, 6, 7 or 8, m is +1 or −1,

X is H, Cl or F,

Y is 1, 2, or 3 and

Z is 3 or 5, with the condition that

X is H, Cl or F, if Z=3 and

X is Cl or F, if Z=5.

From the alkyls class use is made of cyclic, linear or branched methyl, ethyl, propyl, butyl, pentyl, hexyl, heptyl and octyl ligands.

The invention therefore provides a process for preparing perfluoroalkylfluorophosphoranes by an electrochemical synthesis.

The starting substances used according to the invention from the alkylphosphoranes and alkylphosphanes classes form the corresponding phosphonium salts in anhydrous hydrogen fluoride, and these have very good solubility in hydrogen fluoride. Advantageously, solutions with phosphorane or phosphane concentrations from 30 to 60% are not combustible, unlike the pure alkylphosphoranes or alkylphosphanes, and can therefore be used as starting materials which are easy to handle.

It has been found that no explosive substances are formed during the novel electrochemical fluorination of alkylphosphoranes or alkylphosphanes.

The main by-products of the novel electrochemical fluorination are phosphorus pentafluoride and fluoroalkanes, which in turn may be used industrially as ozone-friendly propellant, solvent or synthesis building block.

In contrast to previous assumptions it has been found that it is particularly the unsubstituted trialkylphosphanes having chain lengths of C22 which have particularly high suitability as starting materials for electrochemical perfluorination reactions. Contrary to expectations their stability is very high. Whereas trimethylphosphane is extensively degraded by the electrochemical fluorination, probably due to the cleavage of difluorocarbene, etc., even triethylphosphane is converted with very good yields into triperfluoroethyldifluorophosphorane.

To prepare the compounds according to the invention, use is made of an electrolysis cell which consists of, for example, a cylindrical double-walled vessel, and the material of which, e.g. stainless steel, is stable with respect to the prevailing reaction conditions. The electrolysis cell comprises an electrode package with alternating nickel anodes and cathodes made from HF-resistant materials with in each case an effective surface area of, for example 4.58 $dm^2$ for nickel anodes and nickel cathodes. The electrolysis cell has a commercially available meter to determine the consumption of current during the reaction. To carry out the process, the cell is cooled to temperatures of from −15° C. to 19° C., or temperatures up to 40° C. may be used with increased pressure. Experiments have shown that good results are achieved at from −10° C. to 10° C. However, the temperature preferably used is 0° C., since this temperature is particularly easily maintained, e.g. by ice-water cooling. The cell has a reflux condenser to condense gaseous reaction products. The gas outflow is cooled to temperatures of from −10° C. to −35° C. Cooling to from −15° C. to −33° C. is preferred. It is particularly preferable to carry out operations at −30° C. by using ethanol as cooling medium.

An appropriate amount of liquid hydrogen fluoride is pre-electrolysed for from 2 to 100 hours, depending on moisture content. 48 hours are generally sufficient. The starting materials are used batchwise in the form of 10 to 70% solutions in HF, since these are not combustible. The experiments have shown that the best results are achieved with 30 to 45% solutions. The liquid reaction products are collected at the base of the cell. Gaseous products are conducted away via the reflux condenser and condensed with the aid of two cooling traps in succession which are cooled to from −50° C. to −100° C. The temperature range used is preferably from −60° C. to −85° C., since in this temperature range most of the gaseous products condense. It is very particularly preferable to work at −78° C. with easy cooling by means of dry ice. The process is carried out at a pressure of from 1 to 3 bar. Working at higher pressure requires peripheral equipment specifically designed for this pressure and resulting in considerable costs. For cost-effectiveness reasons it is preferable to work at a small gauge pressure of from 1 to 0.5 bar. The reaction is particularly preferably carried out at atmospheric pressure (1 bar). The electrolysis takes place at a cell voltage of from 4.0 to 6.5 V. The reaction is carried out at a current density of from 0.1 to 3.5 A/dm$^2$. A current density of from 0.2 to 0.6 A/dm$^2$ is generally sufficient. Good results are achieved at a current density of from 0.22 to 0.55 A/dm$^2$. To achieve virtually complete conversion of the starting materials the electrolysis is terminated after from about 80 to 200% of the theoretical electricity throughput. Good conversion is achieved at from 90 to 170% of the theoretical throughput. 95 to 150% throughput proved particularly suitable in the experiments. The liquid reaction product is periodically withdrawn and the volume withdrawn is replaced by adding hydrogen fluoride with new starting material. The total yield is given by the amount of reaction product from the reaction vessel and the reaction product isolated from the cold traps.

The reaction products may, immediately or after purification by distillation, be converted into the corresponding phosphate using lithium fluoride.

The process, which can be carried out at low cost and using simple materials and apparatus, gives, in good yields, products of a quality suitable for use in batteries. This process does not form any explosive or toxic by-products. The by-products do not destroy ozone and can be used as CFHC-substitute propellant gases.

The examples below are intended to describe the invention in greater detail but not to restrict the same.

EXAMPLES

Example 1

Tris(pentafluoroethyl)difluorophosphorane (III)

The compound tris(pentafluoroethyl)difluorophosphorane was prepared by electrochemical fluorination of triethylphosphane. A cylindrical double-walled vessel made from stainless steel with a total volume of 360 cm$^3$ served as electrolysis cell. The electrolysis cell has an electrode package of alternating nickel anodes and nickel cathodes with in each case an effective surface of 4.58 dm$^2$. The cell was cooled to 0° C. and had a reflux condenser with gas outflow at −30° C.

310 g of liquid hydrogen fluoride were firstly pre-electrolysed in the cell, and then a total of 158.2 g of a 36% triethylphosphane solution in hydrogen fluoride was added in five portions, as shown in the following table.

| Amount of triethylphosphane solution [g] | Duration of electrolysis [Ah] |
|---|---|
| 27.8 | 0 |
| 30.4 | 81.8 |
| 31.9 | 168.0 |
| 31.1 | 256.4 |
| 37.0 | 371.3 |

Gaseous products were conducted away via the reflux condenser and passed through two fluoropolymer traps cooled to −78° C. The electrolysis took place at a cell voltage of from 4.0 to 5.1 Volt and at a current density of from 0.44 to 0.55 A/dm$^2$, and was terminated after 517 Ah throughput (133.8% of the theoretically required amount). Of the amount of electricity used, about 7% was used for drying the hydrogen fluoride. The liquid reaction product, which collects at the base of the cell, was periodically withdrawn and the volume discharged replaced by adding 131 g of hydrogen fluoride. A total of 146.1 g of a clear liquid was isolated and shown by $^{19}$F and $^{31}$P-NMR spectra to be practically pure tris(pentafluoroethyl)difluorophosphorane. A further 5 g of this compound could be isolated from the traps cooled to −78° C.

The total yield of tris(pentafluoroethyl)difluorophosphorane was therefore 73.5%.

$^{31}$P-NMR spectroscopic data corresponded to those given in the literature (V. J. Semenii et. al., Zh. Obshch. Khim. (Russ.) 1985, Vol. 55, 12 2716–2720).

(III)

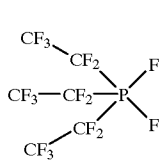

$^{31}$P NMR, ppm: (CD$_3$COCD$_3$ film with 85% H$_3$PO$_4$ as standard),

−47.95 tsep $J^1_{P,F}$=1003 Hz $J^2_{P,F}$=122 Hz $^{19}$F NMR, ppm: (CD$_3$COCD$_3$ film with CCl$_3$F as standard), −49.76 dm (2F, PF$_2$)

−82.27 t (9F, 3CF$_3$)

113.81 dt (6F, 3CF$_2$)

$J^1_{P,F}$=1003 Hz $J^2_{P,F}$−122 Hz $J^3_{F,F}$=12.5 Hz $J^4_{F,F}$=9.5 Hz

Example 2

Tris(nonafluorobutyl)difluorophosphorane (IV)

Tris(nonafluorobutyl)difluorophosphorane was prepared by electrochemical fluorination of tributylphosphine. In this case the electrolysis cell had a volume of 1.5 liters and effective anode and cathode surface areas of in each case 15.6 dm². The cell temperature was 0° C. and the temperature of the reflux condenser was −20° C.

1125 g of liquid hydrogen fluoride was preelectrolysed for 100 hours in the cell and then 268.0 g of tributylphosphine in 34.8 or, respectively 43.6% solution in hydrogen fluoride were added in 7 portions, as listed in the following table.

| Amount of tributylphosphine [g] | Duration of electrolysis [Ah] |
|---|---|
| 41.8 | 0 |
| 38.0 | 291.3 |
| 38.0 | 623.8 |
| 35.1 | 930.6 |
| 41.8 | 1430.0 |
| 35.8 | 1939.0 |
| 37.5 | 2414.9 |

The electrolysis voltage was from 4.5 to 5.2 V (cell voltage), the current density was 0.32 A/dm² and the total use was 2918.4 Ah (146.5% of theoretical). Of the entire amount of electricity used, about 10% was used for drying the electrolyte. The liquid electrolysis products which separated from the hydrogen fluoride solution were withdrawn in portions from the base of the cell, and the volume was held constant by adding supplementary hydrogen fluoride (total amount 1164 g). A total of 470 g of clear liquid was obtained as electrolysis product and $^{19}$F and $^{31}$P spectra showed this to be practically pure tris(nonafluorobutyl)-difluorophosphorane, corresponding to a yield of 48.8%.

The NMR data correspond to the data known from the literature for tris(nonafluorobutyl)difluorophosphorane.
$^{31}$P NMR, ppm: (CD$_3$COCD$_3$ film with 85% H$_3$PO$_4$ as standard),
 −43.50 tsep
 $J^1_{P,F}$=1049.8 Hz $J^2_{P,F}$=125 Hz
$^{19}$F NMR, ppm: (CD$_3$COCD$_3$ film with CCl$_3$F as standard),
 −46.97 dm (2F, PF$_2$)
 −83.36 m (9F, 3CF$_3$)
 109.43 dm (6F, 3CF$_2$)
 121.88 m (6F, 3CF$_2$)
 127.61 m (6F, 3CF$_2$)
 $J^1_{P,F}$=1049 Hz
 $J^2_{P,F}$=124.7 Hz Example 3
Pentafluoroethyltetrafluorophosphorane (V)

49.0 g of dichloroethylphosphane in 63 g of hydrogen fluoride, i.e. 112 g of 43.8% solution, were added during the electrolysis in 4 portions, as shown in the following table, to 308 g of pre-electrolysed liquid hydrogen fluoride in the electrolysis vessel of Example 1. The gaseous products were condensed in two polytetrafluoroethylene traps at −78° C.

| Amount of dichloroethylphosphane solution [g] | Duration of electrolysis [Ah] |
|---|---|
| 31.0 | 0 |
| 34.0 | 33.2 |
| 23.0 | 54.3 |
| 24.0 | 84.6 |

The electrolysis was carried out with from 4.5 to 5.4 Volt of cell voltage and with a current density of from 0.22 to 0.44 A/dm² for 118.1 Ah (98.2% of theoretical). 45 g of a solution which comprised about 15 g of pentafluoroethyltetrafluorophosphorane condensed in the cold trap. This corresponded to a yield of 17.7%.

The volatile reaction product was not isolated but converted into the corresponding pentafluoroethylpentafluorophosphate product by adding 2.25 g of lithium fluoride in HF solution. The NMR data correspond to the data known from the literature for pentafluoroethyltetrafluorophosphorane.
$^{31}$P NMR, ppm: (CD$_3$COCD$_3$ film with 85% H$_3$PO$_4$ as standard)
 −40° C.
 −54.37 ppm Example 4
Tris(heptafluoropropyl)difluorophosphorane (VI)

The compound tris(heptafluoropropyl) difluorophosphorane was prepared by electrochemical fluorination of tripropylphosphane. A cylindrical double-walled vessel made from stainless steel with a total volume of 310 cm³ served as electrolysis cell. The electrolysis cell has an electrode package of alternating nickel anodes and nickel cathodes with in each case an effective surface of 3.75 dm². The cell was cooled to 0° C. and had a reflux condenser with gas outflow at −25° C.

230 g of liquid hydrogen fluoride were firstly pre-electrolysed in the cell, and then a total of 133.0 g of a 37.6% tripropylphosphane solution in hydrogen fluoride was added in four portions, as shown in the following table.

| Amount of tripropylphosphane solution [g] | Duration of electrolysis [Ah] |
|---|---|
| 33.0 | 0 |
| 31.0 | 91.8 |
| 32.0 | 189.8 |
| 37.0 | 282.3 |

The electrolysis took place at a cell voltage of from 4.0 to 5.1 Volt and at a current density of from 0.37 to 0.53 A/dm², and was terminated after 476.3 Ah throughput (129.4% of the theoretically required amount). Of the amount of electricity used, about 5% was used for drying the hydrogen fluoride. The liquid react on product, which collects at the base of the cell, was periodically withdrawn and the volume discharged replaced by adding 135 g of hydrogen fluoride. A total of 95.6 g of a clear liquid was isolated and shown by $^{19}$F and $^{31}$P-NMR spectra to be practically pure tris (heptafluoropropyl)-difluorophosphorane. The yield of tris (heptafluoropropyl)-difluorophosphorane was 53.2%. The $^{19}$F and $^{31}$P NMR spectroscopic data correspond to those in the literature (V. J. Semenii et al., Zh. Obshch. Khim. (Russ.) 1985, Vol. 55, 12, 2716–2720):

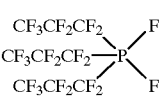

(VI)

$^{31}$P, ppm: (CD$_3$COCD$_3$ film with 85% H$_3$PO$_4$ as standard),
 −43.89 tsep
 $J^1_{P,F}$=1041 Hz
 $J^2_{P,F}$=123.9 Hz
$^{19}$F NMR, ppm: (CD$_3$COCD$_3$ film with CCl$_3$F as standard), −47.42 dm (2F, PF$_2$)
−82.49 m (9F, 3CF$_3$)
−110.40 dm (6F, 3CF$_2$)
−125.77 s (6F, 3CF$_2$)
J$^1$P,F=1040 Hz
J$^2$P,F=124.6 Hz
J$^3$F,F=14.0 Hz Example 5
Tris(nonafluoroisobutyl)difluorophosphorane (VII)

The compound tris(nonafluoroisobutyl) difluorophosphorane was prepared by electrochemical fluorination of tris(isobutyl)phosphane. In this case he electrolysis cell had a volume of 1.5 liters and effective anode and cathode surfaces of in each case 15.6 dm$^2$. The cell was cooled to 0° C. and had a reflux condenser with gas outflow at −20° C.

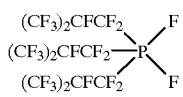 (VII)

$^{31}$P NMR, ppm: (CD$_3$COCD$_3$ film with 85% H$_3$PO$_4$ as standard),
−41.35 tsep
J$^1_{P,F}$=1086 Hz
J$^2_{P,F}$=125.0 Hz
$^{19}$F NMR, ppm: (CD$_3$COCD$_3$ film with CCl$_3$F as standard),
−45.98 dm (2F, PF$_2$)
−74.07 m (18F, 6CF$_3$)
99.20 dm (6F, 3CF$_2$)
180.49 m (3F, 3CF$_2$)
J$^1_{P,F}$=1087 Hz
J$^2_{P,F}$=124.9 Hz 1075 g of liquid hydrogen fluoride were firstly pre-electrolysed in the cell, and then a total of 499.0 g of a 42.9% tri(isobutyl)phosphane solution in hydrogen fluoride was added in five portions, as shown in the following table.

| Amount of tris(isobutyl)phosphane solution [g] | Duration of electrolysis [Ah] |
| --- | --- |
| 104.0 | 0 |
| 96.0 | 315.2 |
| 102.0 | 699.9 |
| 99.0 | 983.6 |
| 98.0 | 1373.4 |

The electrolysis took place at a cell voltage of from 4.5 to 5.5 Volt and at a current density of from 0.20 to 0.35 A/dm$^2$, and was terminated after 2377.2 Ah throughput (149.5% of the theoretically required amount). Of the amount of electricity used, about 9% was used for drying the hydrogen fluoride. The liquid reaction product which separates from the hydrogen fluoride solution was periodically drawn off from the base of the cell and the volume was held constant by adding supplementary hydrogen fluoride (total amount 690 g). A total of 440 g of a clear fluid was isolated and was shown by $^{19}$F and $^{31}$P NMR spectra to be a mixture of tris(nonafluoroisobutyl)difluorophosphorane, tris-(nonafluorobutyl)difluorophosphorane and nonafluorobutyl [bis(nonafluoroisobutyl)]difluorophosphorane. The yield was 57.2%. This mixture comprises about 10% of the isomers with one or two hydrogen atoms. Fractionated distillation in a Teflon apparatus allows tris (nonafluoroisobutyl)difluorophosphorane to be isolated as the main fraction.

What is claimed is:

1. Process for preparing perfluoroalkylfluorophosphoranes of the general formula

 (I)

where
n is 1, 2, 3, 4, 5, 6, 7 or 8
m is +1 or −1 and
y is 1, 2 or 3,
where the ligands (C$_n$F$_{2n+m}$) may be identical or different, characterized in that the electrochemical fluorination of alkylphosphoranes or of alkylphosphanes with identical or different, linear, branched or cyclic alkyl substituents on the phosphorus is carried out in anhydrous HF at a cell temperature of from −15° C. to 40° C. at a pressure of from 1 to 3 bar, at a cell voltage of from 4.0 to 6.5 V and at a current density of from 0.1 to 3.5 A/dm$^2$.

2. Process according to claim 1, characterized in that the fluorination is carried out at from −10° C. to 10° C.

3. Process according to claim 1, characterized in that the fluorination is carried out at 0° C.

4. Process according to claim 1, characterized in that the fluorination is carried out at a pressure of from 1 to 0.5 bar.

5. Process according to claim 1, characterized in that the fluorination is carried out at atmospheric pressure.

6. Process according claim 1, characterized in that the reaction is carried out by a current density of from 0.2 to 3.5 A/dm$^2$.

7. Process according claim 1, characterized in that the reaction is carried out by a current density of from 0.22 to 0.55 A/dm$^2$.

* * * * *